United States Patent [19]

Detalle et al.

[11] Patent Number: 4,749,172
[45] Date of Patent: Jun. 7, 1988

[54] DEVICE FOR DETECTING THE WEAR OF BRICKS FOR BLOWING FLUIDS INTO LIQUID METALS

[76] Inventors: Pol Detalle; Richard Detalle, both of 11, rue Edouard Herriot, F-54600 Villers les Nancy, France

[21] Appl. No.: 937,303

[22] Filed: Dec. 3, 1986

[30] Foreign Application Priority Data

Dec. 3, 1985 [FR] France ............... 85 17880

[51] Int. Cl.⁴ .................................................. C21B 7/24
[52] U.S. Cl. ...................... 266/99; 266/220; 374/7
[58] Field of Search ............ 266/99, 78, 93, 92, 266/80, 81, 90, 220, 217; 73/86; 374/7

[56] References Cited

U.S. PATENT DOCUMENTS

| | | | |
|---|---|---|---|
| 3,490,755 | 1/1970 | Lutgen | 266/220 |
| 3,856,284 | 12/1974 | Hoyer | 266/220 |
| 4,248,809 | 2/1981 | Sakai et al. | 73/86 |
| 4,249,719 | 2/1981 | Knuppel et al. | 266/99 |

FOREIGN PATENT DOCUMENTS 0060069 9/1982 European Pat. Off. ............. 266/99
0648343 2/1979 U.S.S.R. ............................. 266/220

*Primary Examiner*—L. Dewayne Rutledge
*Assistant Examiner*—S. Kastler
*Attorney, Agent, or Firm*—Owen, Wickersham & Erickson

[57] ABSTRACT

The detection device comprises at least two electrically conductive elements (2, 4) arranged outside the refractory brick (1), at least one (4) of the two conductive elements from the rear face of the brick to a predetermined distance from the front face, in contact with the liquid metal, and the two conductive elements being connected to an electrical detection circuit (8, 9), in such a way that when the wear of the brick (1) reaches the end of the conductive element (4) the two conductive elements (2, 4) are put into contact with one another by the liquid metal, and this can be detected on the indicator instrument (9).

The invention is used especially in steel metallurgy.

6 Claims, 1 Drawing Sheet

DEVICE FOR DETECTING THE WEAR OF BRICKS FOR BLOWING FLUIDS INTO LIQUID METALS

The present invention relates to a device for monitoring the wear of bricks for blowing fluids into liquid metals, especially for introducing gases, liquids or powders into molten steel.

At various stages in the production of metals, particularly steel, the metallurgist often has to introduce a neutral or reactive gas, for example in order to prevent the complete or partial solidification of the molten mass, to cause or promote chemical reactions, to prevent the casting channels from being obstructed, to ensure complete or partial reheating of the molten mass or for any other purpose.

To this end, a refractory component called a blast brick or blast nozzle is generally used, and this is placed in the bottom or wall of the metallurgical vessel, which can be, for example, a furnace, a tundish, a refining ladle, a distributor, a system for closing the casting channels, for discharge or for solidification, etc. This refractory component is in contact with the liquid metal and is subject to more or less rapid wear.

It is important for the operator to know the degree of wear reached by the blast brick, so that, in the event of complete wear of the brick, the metal can be prevented from pushing out of the vessel, thereby seriously endangering the operators and the surrounding installations.

Various methods have been adopted to monitor the wear of such a blast brick, but the disadvantage of all of them is that they employ devices placed inside the brick, this having many disadvantages in terms of its manufacture.

The object of the present invention is to develop a device making it possible to detect the wear of a blast brick, without the manufacture of the latter being appreciably affected by the presence on/in this device.

According to the invention, this result is obtained by means of a device for detecting the wear of blast bricks, which comprises a first and a second electrically conductive element which are placed outside the brick and are electrically insulated from one another and which extend from the rear face of the brick towards the front face of the brick in contact with the liquid metal. At least a first of the two electrically conductive elements ends at a distance from the front face of the brick, corresponding to a degree of wear to be detected, whilst the second of the two electrically conductive elements can extend further in the direction of the front face of the brick. The two electrically conductive elements are connected at the rear of the brick to an electrical indicator device in series with a current source.

Because the electrically conductive elements are arranged outside the blast brick, the manufacture of the actual blast brick from refractory material is not affected by the presence of the electrically conductive elements which are attached after the actual brick has been manufactured. Nevertheless, when the wear of the brick reaches a degree predetermined by the distance separating the first electrically conductive element from the front face of the brick, the two electrically conductive elements are put in contact with one another by the conductive liquid metal, so that the indicator device is triggered.

The indicator device can be a device transmitting any signal, for example a lamp, a siren, a galvanometer, a numerical indicator, etc. Particularly with the use of a galvanometer which, in series with the electrical current source, forms an ohmmeter indicating the electrical resistance between the two conductive elements, it is advantageous to connect the electrical resistor of predetermined value between the two electrically conductive elements, directly at the rear of the brick.

As a result of this assembly, as long as the brick is not worn to the degree determined by the first electrically conductive element, the galvanometer indicates the value of this so-called calibrating resistor. This reading guarantees that the entire circuit through which the current flows is sound. In fact, any break or poor contact results in the indication of a very high or infinite resistance on the galvanometer. On the other hand, when the wear of the brick brings the molten metal in contact with the two electrically conductive elements, the calibrating resistor is short-circuited, and the galvanometer indicates a zero resistance which corresponds to a predetermined wear of the blast brick.

In the present state of the art, blast bricks made of permeable refractory material usually have a metal casing which surrounds them on their lateral face and on the rear face, and a fluid feed pipe connected to the rear of this casing so as to open out in the brick. According to a preferred embodiment of the invention, this metal casing forms the second of the two electrically conductive elements, and the first electrically conductive element consists of another metal casing surrounding the first casing from the rear face up to a distance from the front face and being electrically insulated from the first casing. It is therefore sufficient, in this case, to attach a partial casing to a blast brick already provided with a complete casing, in order to produce a blast brick equipped with a wear detection device.

If the aim is to detect more than one degree of wear of the brick, the detection device possesses, in addition to a first and a second electrically conductive element, at least one third conductive element ending at a distance from the front face of the brick which is shorter than that at which the first conductive element ends, this distance corresponding to a second degree of wear to be detected. So that, in this case, the different degrees of wear can be indicated on one and the same instrument, for example a galvanometer in series with a current source, it is advantageous to connect all the electrically conductive elements in one and the same circuit comprising a galvanometer and a current source by inserting an electrical resistor of predetermined value between every two conductive elements.

Thus, as long as the first degree of wear has not been reached, the galvanometer indicates the value of all the resistors inserted between the conductive elements. When the first degree of wear is reached, the liquid metal short-circuits the resistor inserted between the first and second conductive elements, thereby changing the reading given by the galvanometer. When the second degree of wear is reached, the resistor is inserted between the second and third conductive elements is likewise short-circuited.

The number of degrees of wear to be detected can, of course, be greater than two, if a higher number of electrically conductive elements is used.

Two non-limiting exemplary embodiments of the subject of the invention will be described below in more detail with reference to the accompanying drawings; in the drawings.

Figure 1:
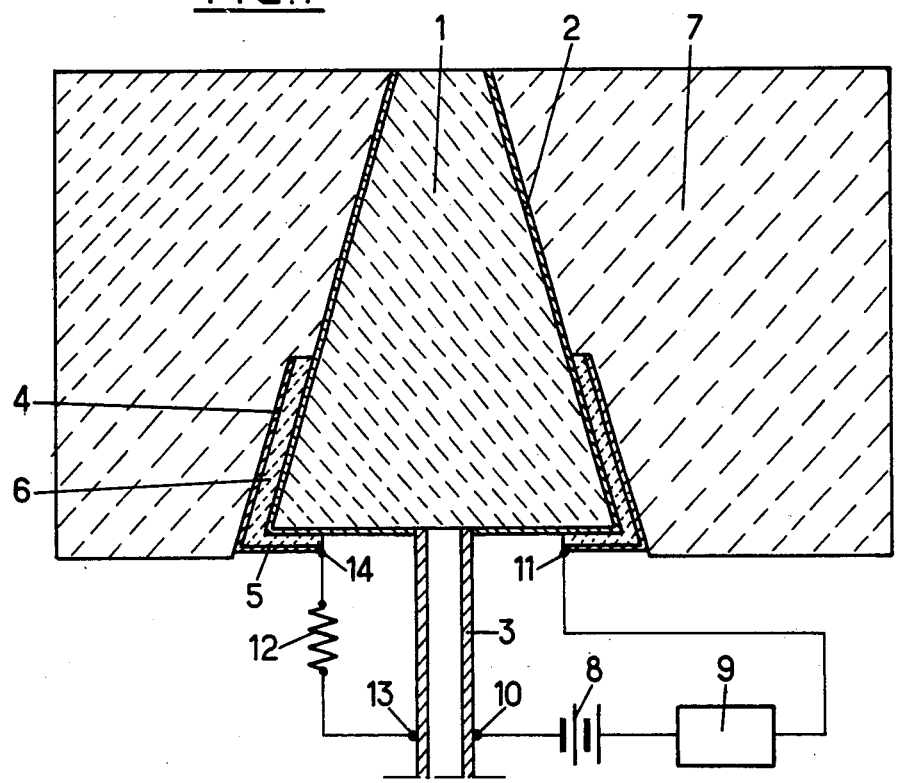
FIG. 1 is a diagrammatic section through an embodiment of a device for detecting one degree of wear.

According to FIG. 1, a frustoconical blast brick 1 permeable to the blowing gas is surrounded in the conventional way with a sheet-metal casing 2 on its lateral surface and on its large base. A metal gas feed pipe 3 is connected in sealed manner to the casing 2 substantially in the middle of the large base of the brick 1. The small base of the brick 1 is free.

From its large base, the casing 2 is surrounded at a distance, over some of the height, by a likewise frustoconical partial metal casing 4 which has a turned-in piece 5 on the large base. The two casings 2 and 4 are separated from one another by a refractory electrical insulator 6.

The blast brick as a whole, formed in this way, is incorporated in a support 7 which is likewise formed by a refractory brick.

The blast brick 1 together with its support 7 is intended to be mounted in the bottom or wall of a metallurgical vessel, in such a way that the front face of the brick 1 corresponding to the small base of the latter is in contact with the liquid metal contained in the vessel.

The two metal casings 2 and 4 are connected to an electrical detection circuit comprising a current source 8 and an indicator instrument 9, for example a galvanometer, which are connected in series. For this purpose, one terminal of the current source 8 is connected via a conductor, by means of a weld 10, to the gas feed pipe 3 which is itself connected to the casing 2, whilst one terminal of the indicator instrument 9 is connected to the casing 4 by means of a conductor and a weld 11, the source 8 and the instrument 9 being connected to one another by means of their other terminals.

Furthermore, a calibrating resistor 12 is connected between the two casings 2 and 4, this resistor likewise being connected to the pipe 3 by means of a weld 13 and to the casing 4 by means of a weld 14.

The two casings 2 and 4 thus constitute two electrodes for detecting the wear of the brick 1. In fact, as long as the brick 1 is not worn up to the casing 4, the two casing 2 and 4 are not in electrical contact with one another, and the galvanometer 9 gives a reading corresponding to the value of the calibrating resistor 12.

The casing 2 melts in proportion to the progress of the wear of the brick 1. When the wear of the brick 1 reaches the upper end of the casing 4, the liquid metal comes into contact with the two casings 2, 4 and thus short-circuit the resistor 12, so that the resistance of the circuit becomes zero, this being detected by the instrument 9. The latter thus gives a reading corresponding to a predetermined wear of the blast brick 1.

Figure 2:
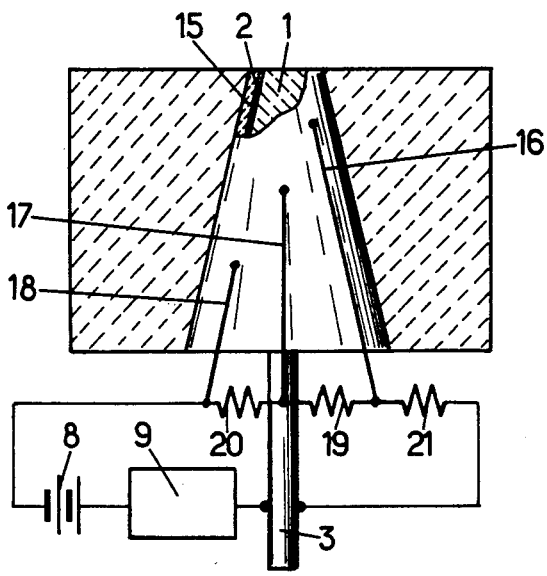
FIG. 2 is a diagrammatic view of a device for detecting three degrees of wear.

FIG. 2 shows diagrammatically a blast brick with a device for detecting three degress of wear.

Here, the casing 2, which surrounds the refractory brick 1 over the full height, as in FIG. 1, and which has a gas feed pipe 3 at the large base, is surrounded over its entire height by a layer of refractory electrical insulator 15. Attached to the outside of this insulator layer 15 are three electrically conductive elements 16, 17, 18 distributed over the periphery and extending from the rear face of the brick up to different distances from the front face of the latter, the element 16 being the longest and the element 18 the shortest.

At the rear of the brick, the three metal conductive elements 16, 17, 18 are connected to one another by means of a resistor 19 inserted between the conductive elements 16 and 17 and a resistor 20 inserted between the conductive elements 17 and 18. Moreover, the conductive element 18 is connected to one terminal of a series connection comprising a current source 8 and an indicator instrument 9, such as a galvanometer, the other terminal of which is connected to a gas feed pipe 3. In turn, the conductive element 16 is connected to the gas feed pipe 3 by means of a resistor 21 which is thus inserted between the casing 2 and the conductive element 16.

During operation, as long as the wear of the brick 1 has not reached the front end of the longest conductive element 16, the instrument 9 gives a reading which corresponds to the three resistors 19, 20 and 21 in series.

When the wear of the brick 1 has reached the end of the conductive element 16, the liquid metal puts the element 16 into contact with the casing 2, thus shortcircuiting the resistor 21. The instrument 9 then gives a reading corresponding to a first degree of wear.

When the wear of the brick 1 reaches the front end of the conductive element 17, the liquid metal likewise makes contact between the element 17 and the element 16, so that the resistor 19 is likewise shortcircuited and the instrument 9 gives a reading corresponding to a second degree of wear.

When the wear of the brick 1 reaches the front end of the conductive element 18, the liquid metal likewise makes contact between the element 18 and the element 17, thereby likewise short-circuiting the resistor 20. The resistance of the circuit is then zero and the reading given by the instrument 9 corresponds to a third degree of wear.

It is appropriate to note that the embodiments described above and illustrated in the accompanying drawings have been given only as a non-limiting illustration, and that many modifications and alternative forms are possible within the scope of the invention.

Thus, the invention can also be used in blast bricks which are not surrounded by a metal casing 2, in which case it is sufficient to attach to the lateral surface of the refractory brick two or more conductive elements insulated electrically from one another and connected to an electrical resistance detection circuit similar to those described.

Furthermore, instead of using an indicator instrument, such as a galvanometer 9, it is also possible to use devices transmitting signals, for example light signals (lamps) and sound signals (sirens), numerical indicators or any other suitable monitoring and/or alarm devices.

We claim:

1. Device for detecting the wear of a brick having a front face and a rear face and means for blowing fluids into liquid metals. comprising first and second electrically conductive elements which are placed outside the brick and are insulated electrically from one another and which extend from the rear face of the brick towards the front face of the brick, in contact with the liquid metal, said first of the two electrically conductive elements ending at a distance from the front face of the brick corresponding to a degree of wear detected, whilst the second of the two electrically conductive elements extends at least as far in the direction of the front face of the brick, the two electrically conductive elements being connected at the rear of the brick to an electrical indicator instrument in series with a current source.

2. Device according to claim 1, wherein an electrical resistor of predetermined value lies between the two electrically conductive elements.

3. Device according to claim 1 wherein the second of the two electrically conductive elements comprises a metal casing surrounding the brick from the rear face up to the front face, and the first electrically conductive element comprises another metal casing surrounding the first metal casing from the rear face to a distance from the front face and being eletrically insulated from the first casing.

4. Device according to claim 2, wherein the second of the two electrically conductive elements comprises a metal casing surrounding the brick from the rear face up to the front face, and the first electrically conductive element comprises another metal casing surrounding the first casing from the rear face to a distance from the front face and being electrically insulated from the first casing.

5. Device for detecting the wear of a brick having a front face and a rear face and means for blowing fluids into liquid metals, comprising
   first and a second electrically conductive elements which are placed outside the brick and are insulated electrically from one another and which extend from the rear face of the brick towards the front face of the brick, in contact with the liquid metal, said first of the two electrically conductive elements ending at a distance from the front face of the brick corresponding to a degree of wear detected, whilst the second of the two electrically conductive elements can extend further in the direction of the front face of the brick,
   the two electrically conductive elements being connected at the rear of the brick to an electrical indicator instrument in series with a current source, and
   at least one third conductive element ending at a distance from the front face of the brick which is shorter than that at which the first conductive element ends,
   all the electrically conductive elements being connected to one and the same circuit comprising in series a current source and an indicator instrument, and
   an electrical resistor of predetermined value inserted between every two conductive elements.

6. Device for detecting the wear of a brick having a front face and a rear face and means for blowing fluids into the liquid metals, comprising
   first and a second electrically conductive elements which are placed outside the brick and are insulated electrically from one another and which extend from the rear face of the brick towards the front face of the brick, in contact with the liquid metal,
   said first of the two electrically conductive elements ending at a distance from the front face of the brick corresponding to a degree of wear detected,
   whilst the second of the two electrically conductive elements can extend further in the direction of the front face of the brick,
   the two electrically conductive elements being connected at the rear of the brick to an electrical indicator instrument in series with a current source,
   an electrical resistor of predetermined value between the two electrically conductive elements, and
   at least one third conductive element ending at a distance from the front face of the brick which is shorter than that at which the first conductive element ends,
   all the electrically conductive elements being connected to one and the same circuit comprising in series a current source and an indicator instrument, and
   an electrical resistor of predetermined value inserted between every two conductive elements.

* * * * *